US009107922B2

(12) United States Patent
Tung

(10) Patent No.: US 9,107,922 B2
(45) Date of Patent: Aug. 18, 2015

(54) PYRIMIDINECARBOXAMIDE DERIVATIVES

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 13/808,508

(22) PCT Filed: Jul. 13, 2011

(86) PCT No.: PCT/US2011/043872
§ 371 (c)(1),
(2), (4) Date: Jan. 4, 2013

(87) PCT Pub. No.: WO2012/009446
PCT Pub. Date: Jan. 19, 2012

(65) Prior Publication Data
US 2013/0109660 A1 May 2, 2013

Related U.S. Application Data

(60) Provisional application No. 61/364,918, filed on Jul. 16, 2010.

(51) Int. Cl.
*C07D 413/12* (2006.01)
*A61K 31/506* (2006.01)
*C07B 59/00* (2006.01)
*A61K 45/06* (2006.01)

(52) U.S. Cl.
CPC ............... *A61K 31/506* (2013.01); *A61K 45/06* (2013.01); *C07B 59/002* (2013.01); *C07D 413/12* (2013.01)

(58) Field of Classification Search
None
See application file for complete search history.

(56) References Cited

U.S. PATENT DOCUMENTS

| 5,304,121 | A | 4/1994 | Sahatjian |
| 5,886,026 | A | 3/1999 | Hunter et al. |
| 6,099,562 | A | 8/2000 | Ding et al. |
| 6,221,335 | B1 | 4/2001 | Foster |
| 6,440,710 | B1 | 8/2002 | Keinan et al. |
| 6,603,008 | B1 | 8/2003 | Ando et al. |
| 6,803,031 | B2 | 10/2004 | Rabinowitz et al. |
| 7,169,780 | B2 | 1/2007 | Crescenzi et al. |
| 7,517,990 | B2 | 4/2009 | Ito et al. |
| 7,687,509 | B2 | 3/2010 | Harbeson |
| 8,318,754 | B2 | 11/2012 | Harbeson |
| 2007/0082929 | A1 | 4/2007 | Gant et al. |
| 2007/0197695 | A1 | 8/2007 | Potyen et al. |
| 2008/0103122 | A1 | 5/2008 | Veltri |

FOREIGN PATENT DOCUMENTS

| WO | WO 95/26325 | 10/1995 |
| WO | WO 03/097593 | 11/2003 |
| WO | WO 2005/087767 | 9/2005 |
| WO | WO 2005/087768 | 9/2005 |
| WO | WO 2006/060711 | 6/2006 |
| WO | WO 2006/060712 | 6/2006 |
| WO | WO 2006/103399 | 10/2006 |
| WO | WO 2006/107478 | 10/2006 |
| WO | WO 2007/118651 | 10/2007 |
| WO | WO 2007/120589 | 10/2007 |
| WO | WO 2009/009531 | 1/2009 |
| WO | WO 2009/088729 | 7/2009 |

OTHER PUBLICATIONS

"Clinical Trial to Assess the Efficacy of Darunavir/Ritonavir (DRV/r), Etravirine (ETV) and Raltegravir (MK-0518) in HIV Patients with Resistant Viruses (ANRS139 TRIO)," accessed Nov. 15, 2013, 4 pages, http://www.clinicaltrials.gov/ct/show/NCT00460382.
"Efficacy and Tolerance of the Switch From Enfuvirtine to Raltegravir in Antiretroviral Therapy Regimen in HIV Patients with Undetectable Viral Load (EASIER)," accessed Nov. 15, 2013, 4 pages, http://www.clinicaltrials.gov/ct/show/NCT00454337.
Baillie, "The use of stable isotopes in pharmacological research," *Pharmacological Review*, 1981, 33(2):81-132.
Blake et al., "Studies with Deuterated Drugs," *J. Pharm Sci*, 1975, 64:367-391.
Cherrah et al., "Study of deuterium isotope effects on protein binding by gas chromatography/mass spectrometry. Caffeine and deuterated isotopomers," *Biomedical and Environmental Mass Spectrometry*, 1987, 14:653-657.
Demko et al., "Preparation of 5-substituted 1H-tetrazoles from nitriles in water," *J. Org. Chem.*, 2001, 66(24):7945-7950.
Dyck et al., "Effects of deuterium substitution on the catabolism of β-Phenylethylamine: An in vivo study," *J. Neurochem.*, 1986, 46:399-404.
Fisher et al., "The Complexities Inherent in Attempts to Decrease Drug Clearance by Blocking Sites of CYP-mediated Metabolism," *Curr. Opin. Drug Discovery Development*, 2006, 9(1):101-109.
Foster, "Deuterium isotope effects in studies of drug metabolism," *Trends in Pharmacological Sciences*, 1984, 5:524-527.
Foster, "Deuterium Isotope Effects in the Metabolism of Drugs and Xenobiotics: Implications for Drug Design," *Advances in Drug Research*, 1985, 14:2-41.
Freireich et al., "Quantitative comparison of toxicity of anticancer agents in mouse, rat, hamster, dog, monkey, and man," *Cancer Chemother. Reports*, 1966, 50(4):219-244.
Fukuto et al., "Determination of the Mechanism of Demethylenation of (Metylenedioxy) phenyl Compounds by Cytochrome P450 Using Deuterium Isotope Effects," *J. Med. Chem*, 1991, 34:2871-2876.
Gannes et al., "Natural abundance variations in stable isotopes and their potential uses in animal physiological ecology," *Comp. Biochem. Physiol.*, 1998, 119A(3):725-737.
Gouyette, Synthesis of deuterium-labelled elliptinium and its use in metabolic studies, *Biomedical and Environmental Mass Spectrometry*, 1988, 15:243-247.
Haskins, "The application of stable isotopes in biomedical research," *Biomedical Mass Spectrometry*, 1982. 9(7):269-277.

(Continued)

*Primary Examiner* — Anna Pagonakis
(74) *Attorney, Agent, or Firm* — Fish & Richardson P.C.

(57) ABSTRACT

This disclosure relates to novel HIV integrase inhibitors their derivatives, pharmaceutically acceptable salts thereof. This disclosure also provides compositions comprising a compound of this disclosure and the use of such compositions in methods of treating HIV infections.

13 Claims, No Drawings

(56) References Cited

OTHER PUBLICATIONS

Honma et al., "The metabolism of roxatidine acetate hydrochloride: liberation of deuterium from the ring piperidine ring during hydroxylation," *Drug Metabolism and Disposition*, 1987, 15(4):551-559.

Horino et al., "Preparation, structure, and unique thermal [2+2], [4+2], and [3+2] cycloaddition reactions of 4-vinylideneoxazolidin-2-one," *Chem. Eur. J.*, 2003, 9(11):2419-2438.

Houston et al., "Prediction of hepatic clearance from microsomes, hepatocytes, and liver slices," *Drug Metab. Rev.*, 1997, 29(4):891-922.

Houston, "Utility of in vitro drug metabolism data in predicting in vivo metabolic clearance," *Biochem. Pharmacol.*, 1994, 47(9):1469-1479.

Isentress (raltegravir) Tablets, Oct. 2007, Merck & Co., 18-page product brochure.

Iwatsubo et al., "Prediction of In Vivo Drug Metabolism in the Human Liver from In Vitro Metabolism Data," *Pharmacol. Ther.*, 1997, 73(2):147-171.

Kempf et al., "Pharmacokinetic Enhancement of Inhibitors of the Human Immunodeficiency Virus Protease by Coadministration with Ritonavir," *Antimicrobial Agents and Chemotherapy*, 1997, 41(3):654-660.

Kushner et al., "Pharmacological Uses and Perspectives of Heavy Water and Deuterated Compounds," *Can. J. Pharmacol.*, 1999, 77:79-88.

Lavéet al., "The Use of Human Hepatocytes to Select Compounds Based on Their Expected Hepatic Extraction Ratios in Humans," *Pharm. Res.*, 1997, 14(2):152-155.

Marcus et al., "HIV: epidemiology and strategies for therapy and vaccination," PubMed Abstract, *Intervirology*, 2002, 45(4-6):260-266.

Miles, "The growing HIF pandemic," PubMed Abstract, *Community Pract.*, ;Aug. 2005, 78(8):292-294.

Obach, "Prediction of Human Clearance of Twenty-nine Drugs from Hepatic Microsomal Intrinsic Clearance Data: An Examination of In Vitro Half-Life Approach and Nonspecific Binding to Microsomes," *Drug Metab. Disp.*, 1999, 27(11):1350-1359.

Pieniaszek et al., "Moricizine Bioavailability via Simultaneous, Dual, Stable Isotope Administration: Bioequivalence Implications," *J Clin Pharmacol.*, 1999;39:817-825.

Sardashti et al., "$^{13}$C and $^{15}$N Chemical Shift Tensors of Para-Substituted Benzonitriles," *J. Phys. Chem.*, 1988, 92(16):4620-4632.

Scientific Tables, *Geigy Pharmaceuticals*, Ardsley, N.Y., 1970, p. 537.

Summa et al., "Discovery of Raltegravir, a Potent, Selective Orally Bioavailable HIV-Integrase Inhibitor for the Treatment of HIV-AIDS Infection," *J. Med. Chem.*, 2008, 51:5843-5855.

Tachibana et al., "Sequential O- and N-acylation protocol for high-yield preparation and modification of rotaxanes: synthesis, functionalization, structure, and intercomponent interaction of rotaxanes," *J. Org. Chem.*, 2006, 71(14):5093-5104.

Tonn et al., "Simultaneous analysis of diphenhydramine and a stable isotope analog($^{2}$H$_{10}$)diphenhydramine using capillary gas chromatography with mass selective detection on biological fluids from chronically instrumented pregnant ewes," *Biological Mass Spectrometry*, 1993, 22:633-642.

Van Heeswijk et al., "Combination of protease inhibitors for the treatment of HIV-1-infected patients: a review of pharmacokinetics and clinical experience," PubMed Abstract, Intivir Ther., Dec. 6, 2001(4):209-229.

Wada and Hanba, "Natural abundance of carbon, nitrogen, and hydrogen isotope ratios in biogenic substances: Present and future," *Seikagaku*, 1994, 66(1):15-29.

Wade, "Deuterium isotope effects on noncovalent interactions between molecules," *Chemico-Biological Interactions*, 1999, 117:191-217.

Wolen, "The application of stable isotopes to studies of drug bioavailability and bioequivalence," *J Clin Pharmacol.*, 1986, 26:419-424.

Authorized Officer Eckhard Baston, International Search Report and Written Opinion of the International Searching Authority in PCT/US2008/069425, mailed Jan. 5, 2009, 8 pages.

Authorized Officer Beate Giffo-Schmitt, International Preliminary Report on Patentability in PCT/US2008/069425, issued Jan. 12, 2010, 6 pages.

International Preliminary Report on Patentability in International Application No. PCT/US2011/043872, mailed Jan. 22, 2013, 7 pages.

International Search Report and Written Opinion in International Application No. PCT/US2011/043872, mailed Oct. 5, 2011.

Browne, "Stable isotope techniques in early drug development: An economic evaluation," J Clin Pharmacol., 1998, 38:213-220.

PYRIMIDINECARBOXAMIDE DERIVATIVES

CROSS-REFERENCE TO RELATED APPLICATIONS

This application is a National Stage application under 35 U.S.C. 371 of International Application No. PCT/US2011/043872, having an International Filing Date of Jul. 13, 2011, which claims the benefit of priority to U.S. Provisional Application Ser. No. 61/364,918, filed on Jul. 16, 2010, which is incorporated by reference herein in its entirety.

TECHNICAL FIELD

This disclosure relates to novel HIV integrase inhibitors, their derivatives and pharmaceutically acceptable salts thereof. This disclosure also provides compositions comprising a compound of this disclosure and the use of such compositions in methods of treating HIV infections.

BACKGROUND

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

AIDS or acquired immune deficiency syndrome is a disease of the immune system caused by the HIV virus. In their December 2006 AIDS epidemic update the Joint United Nations Programme on HIV/AIDS and the World Health Organization reported that 39.5 million people worldwide were infected with HIV. Of that number, 4.3 million people were newly infected in 2006.

Raltegravir is a new drug candidate that shows potent in-vitro activity against HIV-1 strains, including those that are resistant to current anti-retroviral drugs. Raltegravir is also known as MK-0518 and by the chemical names, N4-[(4-fluorophenyl)methyl]-1,6-dihydro-5-hydroxy-1-methyl-2-[1-methyl-1-[[(5-methyl-1,3,4-oxadiazol-2-yl)carbonyl]amino]ethyl]-6-oxo-4-pyrimidinecarboxamide and N-(2-(4-(4-fluorobenzylcarbamoyl)-5-hydroxy-1-methyl-6-oxo-1,6-dihydropyrimidin-2-yl)propan-2-yl)-5-methyl-1,3,4-oxadiazole-2-carboxamide.

Raltegravir inhibits the activity of the HIV-1 integrase. It is approved for the treatment of AIDS (http://www.clinicaltrials.gov/ct/show/NCT00460382; http://www.clinicaltrials.gov/ct/show/NCT00454337).

Despite the beneficial activities of raltegravir, there is a continuing need for new compounds to treat HIV infection.

DEFINITIONS

The term "alkyl" refers to a monovalent saturated hydrocarbon group. $C_1$-$C_7$ alkyl is an alkyl having from 1 to 7 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl, 2-methylpentyl and heptyl.

The term "carbon unit" refers to —$CH_2$— optionally substituted with 1 to 2 $C_1$-$C_3$ alkyls. Examples of carbon units include —$CH_2$—; —$CH(CH_3)$—; —$C(CH_3)_2$—; —$CH(CH_2$—$CH_3)$—; and —$C(CH_2CH_3)_2$—. For the avoidance of doubt, a —$CH_3$ moiety of any alkyl is not included within the definition of a carbon unit. A carbon unit, as the term is used herein, is part of a $C_1$-$C_7$ alkyl.

The term "carbocyclyl" refers to a monocyclic or bicyclic saturated, partially saturated, or aromatic group containing only carbon ring atoms. The term "$C_3$-$C_7$ carbocyclyl" refers to a monocyclic saturated, partially saturated, aromatic or unsaturated group containing between 3 and 7 carbon ring atoms. Examples of saturated groups include cyclopropyl, cyclobutyl, cyclopentyl, and cyclohexyl, cycloheptyl, cis- and trans-decalinyl, and norbornyl. Examples of partially saturated groups include cyclopropenyl, cyclobutenyl, cyclopenentyl, and cyclohexenyl.

The term "aryl" refers to an aromatic carbocyclyl. The term "$C_6$-$C_{10}$ aryl" refers to a monocyclic or bicyclic, aromatic carbocyclyl containing between 6 and 10 ring carbon atoms. Examples of aryl are phenyl and naphthyl.

The term "3-7 membered heterocyclyl" refers to a monocyclic saturated, partially saturated, or aromatic ring containing between 3 and 7 ring atoms, wherein one or more ring atoms is a heteroatom independently selected from N, O, and S. Examples of non-aromatic heterocyclyls include azepanyl, azetidinyl, aziridinyl, imidazolidinyl, morpholinyl, oxazolidinyl, piperazinyl, piperidinyl, pyrazolidinyl, pyrrolidinyl, tetrahydrofuranyl, thiomorpholinyl, and 4-methyl-1,3-dioxol-2-onyl.

The term "heteroaryl" refers to a monovalent aromatic heterocyclyl. A 5 to 6-membered heteroaryl contains between 5 and 6 ring atoms wherein from 1 to 4 ring atoms are heteroatoms independently selected from the group consisting of O, N and S. Examples of heteroaryl groups include furanyl, thiazolyl, isothiazolyl, isoxazolyl, oxazolyl, pyrimidinyl, pyrazolyl, pyridazinyl, pyridinyl, pyrrolyl, thiadiazolyl, thiophenyl, triazinyl, and triazolyl.

A carbocyclyl or heterocyclyl is "benzofused" if it shares a common bond with a benzene ring. The number of atoms referred to in a benzofused carbocylyl or heterocyclyl ring is not intended to include the four atoms of the benzene ring that do not share the common bond. For example, a benzofused $C_3$-$C_7$ carbocyclyl would include a cyclobutyl fused to a benzene ring, and a benzofused 3-7 membered heterocyclyl would include a tetrahydrofuranyl fused to a benzene ring.

The term "carbocyclic ring" refers to a monocyclic hydrocarbon ring system, which may be saturated or unsaturated. Examples include $C_3$-$C_7$ carbocyclic rings.

The term "heterocyclic ring" refers to a monocyclic hydrocarbon ring system, which may be saturated or unsaturated, wherein from 1 to 4 ring atoms are heteroatoms independently selected from the group consisting of O, N and S. Examples include 3 to 7-membered heterocyclic rings.

The term "treat" means decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of raltegravir will inherently contain small amounts of deuterated isotopologues. The concentration of naturally abundant stable hydrogen isotopes, notwithstanding this variation, is small and immaterial as compared to the degree of stable isotopic substitution of compounds of this disclosure. See, for instance, Wada E et al., Seikagaku, 1994, 66:15; Gannes L Z et al., Comp Biochem Physiol Mol Integr Physiol, 1998, 119:725. In a compound of this disclosure, when a particular position is designated as having deuterium, it is understood that the abundance of deuterium at that position is substantially greater than the natural abundance of deuterium, which is 0.015%. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance of D at a specified position in a compound of this disclosure and the naturally occurring abundance of that isotope. The natural abundance of deuterium is 0.015%.

In other embodiments, a compound of this disclosure has an isotopic enrichment factor for each deuterium present at a site designated as a potential site of deuteration on the compound of at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It is understood that the isotopic enrichment factor of each deuterium present at a site designated as a site of deuteration is independent of other deuterated sites. For example, if there are two sites of deuteration on a compound one site could be deuterated at 52.5% while the other could be deuterated at 75%. The resulting compound would be considered to be a compound wherein the isotopic enrichment factor is at least 3500 (52.5%).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

"Substituted with deuterium" refers to the replacement of one or more hydrogen atoms with a corresponding number of deuterium atoms.

Throughout this specification, a variable may be referred to generally (e.g., "each R") or may be referred to specifically (e.g., $R^1$, $R^{2a}$, $R^{2b}$, etc.). Unless otherwise indicated, when a variable is referred to generally, it is meant to include all specific embodiments of that particular variable.

Therapeutic Compounds

Provided herein is a compound of Formula I:

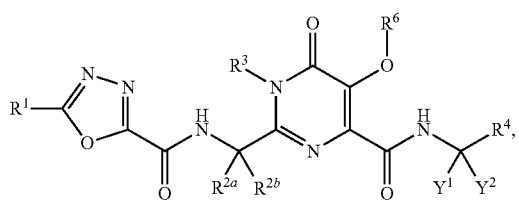

(I)

or a pharmaceutically acceptable salt thereof, wherein:

each of $R^1$, $R^{2a}$, $R^{2b}$, and $R^3$ is independently selected from $CH_3$, $CDH_2$, $CD_2H$, and $CD_3$;

$Y^1$ and $Y^2$ are each independently selected from H and D;

$R^4$ is selected from:

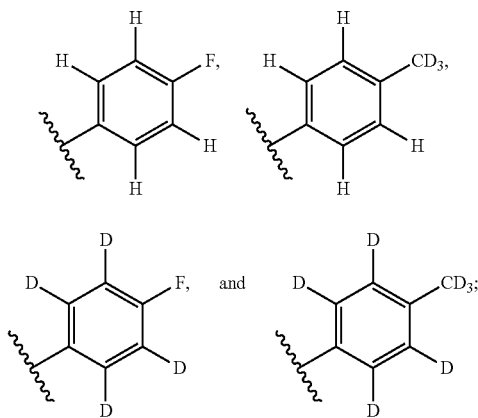

and $R^6$ is selected from the group consisting of —C($R^7$)($R^8$)—O—Z and —(CH$_2$)$_q$—C(O)—$R^{12}$, wherein:

q is 1 or 0;

$R^{12}$ is selected from C$_6$-C$_{10}$ aryl optionally substituted with deuterium, and C$_1$-C$_7$ alkyl optionally substituted with one or two $R^{10}$ and further optionally substituted with deuterium, wherein:

(a)(i) one carbon unit in the C$_1$-C$_7$ alkyl, wherein the carbon unit is bound to a —C(O)— of the —C(O)—C$_1$-C$_7$ alkyl, is optionally replaced with —C(O)—, —O—, —S—, —NH, or —N(C$_1$-C$_3$ alkyl);

a(ii) one carbon unit in the C$_1$-C$_7$ alkyl, wherein the carbon unit is not bound to a —C(O)— of the —C(O)—C$_1$-C$_7$ alkyl, is optionally replaced with —C(O)—, —S(O)—, —S(O)$_2$, —O—, —S—, —NH, or —N(C$_1$-C$_3$ alkyl);

(b)(i) when a first carbon unit in the C$_1$-C$_7$ alkyl is replaced with —C(O)—, —S(O)—, or —S(O)$_2$, a second carbon unit is optionally replaced with —O—, —S—, —NH, or —N(C$_1$-C$_3$ alkyl); and (b)(ii) when a first carbon unit in the C$_1$-C$_7$ alkyl is replaced with —O—, —S—, —NH, or —N(C$_1$-C$_3$ alkyl), a second carbon unit, separated by at least two carbon units from the first carbon unit replaced with —O—, —S—, —NH, or —N(C$_1$-C$_3$ alkyl), is optionally replaced with —O—, —S—, —NH, or —N(C$_1$-C$_3$ alkyl);

each $R^{10}$ is independently a C$_3$-C$_7$ carbocyclyl or a 3-7-membered heterocyclyl, wherein each $R^{10}$ is optionally and independently substituted with C$_1$-C$_3$ alkyl or deuterium and optionally and independently benzofused;

$R^7$ and $R^8$ are each independently hydrogen, deuterium, or C$_1$-C$_3$ alkyl optionally substituted with deuterium; or $R^7$ and $R^8$ taken together with the carbon to which they are attached form a C$_3$-C$_7$ saturated or partially saturated carbocyclic ring or a saturated or partially saturated 3-7-membered heterocyclic ring, wherein the carbocyclic ring or heterocyclic ring is optionally substituted with deuterium; and Z is C$_1$-C$_6$ alkyl optionally substituted with deuterium, with the proviso that the compound of Formula I is none of the following:

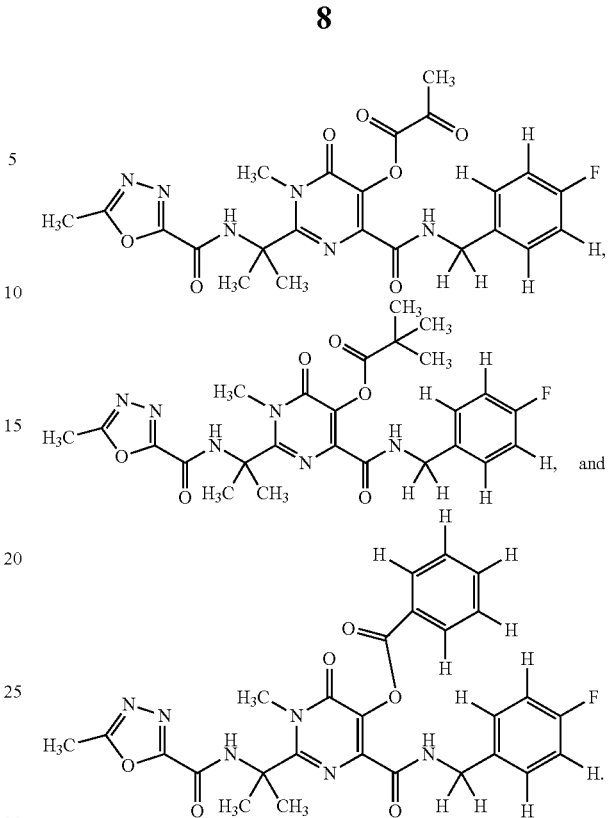

In one embodiment of the compound of Formula I, when each of $Y^1$ and $Y^2$ is H, then at least one of $R^1$, $R^{2a}$, $R^{2b}$, $R^3$ and $R^4$ comprises deuterium. A compound of formula I according to this embodiment is referred to herein as a compound of formula I-A.

In one embodiment of formula I or formula I-A, $R^6$ is —(CH$_2$)$_q$—C(O)—$R^{12}$, wherein q is 1 or 0; and $R^{12}$ is —C$_1$-C$_7$ alkyl optionally substituted with one $R^{10}$ and further optionally substituted with deuterium, wherein each $R^{10}$ is optionally and independently substituted with C$_1$-C$_3$ alkyl or deuterium, and wherein the first and the second carbon units in (b)(ii) are each optionally replaced with —O—. In one embodiment of formula I or formula I-A, $R^6$ is —(CH$_2$)$_q$—C(O)—$R^{12}$, wherein q is 1 or 0; and $R^{12}$ is methyl, ethyl, isopropyl, tert-butyl, or phenyl, each optionally substituted with deuterium. In one aspect of this embodiment of formula I, $R^1$, $R^{2a}$, $R^{2b}$, and $R^3$ are —CH$_3$; $Y^1$ and $Y^2$ are each hydrogen; $R^4$ is

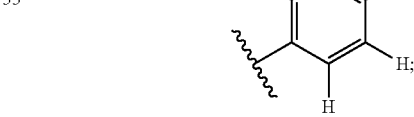

and then $R^{12}$ is substituted with deuterium. In one aspect of this embodiment of formula I-A, $R^{12}$ is substituted with deuterium.

In one embodiment of formula I or formula I-A, $R^{12}$ is isobutyl, neopentyl, isoamyl, —CH$_2$—CH$_2$—O—CH$_3$, —CH$_2$—CH$_2$—CH$_2$—CH$_2$—CH$_3$,

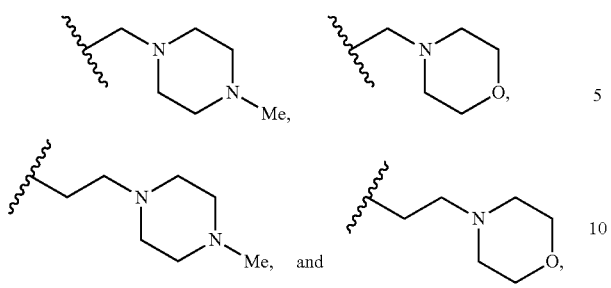
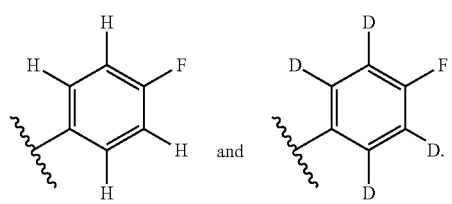

wherein $R^{12}$ and the heterocyclyl substituent of $R^{12}$ are each optionally and independently substituted with deuterium. In one aspect of this embodiment of the compound of formula I, $R^1$, $R^{2a}$, $R^{2b}$, and $R^3$ are —$CH_3$; $Y^1$ and $Y^2$ are each hydrogen; $R^4$ is

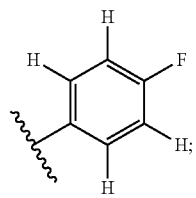

and $R^{12}$ is substituted with deuterium. In one aspect of this embodiment of formula I-A, $R^{12}$ is substituted with deuterium.

In one embodiment of formula I or formula I-A, $R^6$ is —$C(R^7)(R^8)$—O—Z wherein $R^7$ and $R^8$ are each independently hydrogen, deuterium, —$CH_3$, —$CH_2D$, —$CHD_2$, or —$CD_3$; and Z is $C_1$-$C_4$ alkyl optionally substituted with deuterium In one aspect of this embodiment, $R^7$ and $R^8$ are each independently hydrogen, deuterium, —$CH_3$, or —$CD_3$; and Z is ethyl, propyl, isopropyl, isobutyl, sec-butyl, or tert-butyl wherein Z is optionally substituted with deuterium. In one aspect of this embodiment for the compound of formula I, $R^1$, $R^{2a}$, $R^{2b}$, and $R^3$ are —$CH_3$; $Y^1$ and $Y^2$ are each hydrogen; $R^4$ is

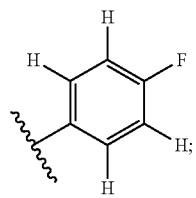

and then $R^6$ comprises deuterium. In one aspect of this embodiment for the compound of formula I-A, $R^6$ comprises deuterium.

In one embodiment, each of $R^1$, $R^{2a}$, $R^{2b}$, and $R^3$ is independently selected from —$CH_3$ and —$CD_3$.

In one embodiment, $Y^1$ and $Y^2$ are the same. In one aspect, each of $Y^1$ and $Y^2$ is hydrogen. In another aspect, each of $Y^1$ and $Y^2$ is deuterium.

In one embodiment, $R^{2a}$ and $R^{2b}$ are the same and are selected from —$CH_3$ and —$CD_3$.

In one embodiment, $R^4$ is selected from

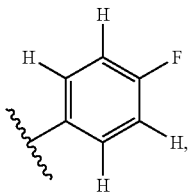

In one embodiment of the compound of formula Ia, $R^4$ is

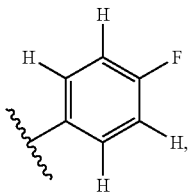

$Y^1$ and $Y^2$ are the same; $R^{2a}$ and $R^{2b}$ are the same; $R^6$ is —$C(O)$—$CH_2$—$CH_2$—O—$CH_3$, and the compound is selected from any one of the compounds set forth in the table below:

| Compound | $R^1$ | $R^{2a}/R^{2b}$ | $R^3$ | $Y^1/Y^2$ |
|---|---|---|---|---|
| 101 | $CD_3$ | $CH_3$ | $CH_3$ | H |
| 102 | $CH_3$ | $CD_3$ | $CH_3$ | H |
| 103 | $CH_3$ | $CH_3$ | $CD_3$ | H |
| 104 | $CH_3$ | $CH_3$ | $CH_3$ | D |
| 105 | $CD_3$ | $CD_3$ | $CH_3$ | H |
| 106 | $CD_3$ | $CH_3$ | $CD_3$ | H |
| 107 | $CD_3$ | $CH_3$ | $CH_3$ | D |
| 108 | $CH_3$ | $CD_3$ | $CD_3$ | H |
| 109 | $CH_3$ | $CD_3$ | $CH_3$ | D |
| 110 | $CH_3$ | $CH_3$ | $CD_3$ | D |
| 111 | $CD_3$ | $CD_3$ | $CD_3$ | H |
| 112 | $CD_3$ | $CH_3$ | $CD_3$ | D |
| 113 | $CH_3$ | $CD_3$ | $CD_3$ | D |
| 114 | $CD_3$ | $CD_3$ | $CD_3$ | D |

In one embodiment of the compound of formula Ia, $R^4$ is

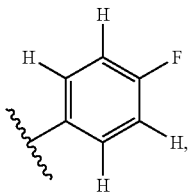

$Y^1$ and $Y^2$ are the same; $R^{2a}$ and $R^{2b}$ are the same; $R^6$ is —$C(O)$—$CH_2$—$CH_2$—O—$CH_2$—$CH_2$—O—$CH_3$; and the compound is selected from any one of the compounds set forth in the table below.

| Compound | $R^1$ | $R^{2a}/R^{2b}$ | $R^3$ | $Y^1/Y^2$ |
|---|---|---|---|---|
| 115 | $CD_3$ | $CH_3$ | $CH_3$ | H |
| 116 | $CH_3$ | $CD_3$ | $CH_3$ | H |
| 117 | $CH_3$ | $CH_3$ | $CD_3$ | H |
| 118 | $CH_3$ | $CH_3$ | $CH_3$ | D |

-continued

| Compound | $R^1$ | $R^{2a}/R^{2b}$ | $R^3$ | $Y^1/Y^2$ |
|---|---|---|---|---|
| 119 | $CD_3$ | $CD_3$ | $CH_3$ | H |
| 120 | $CD_3$ | $CH_3$ | $CD_3$ | H |
| 121 | $CD_3$ | $CH_3$ | $CH_3$ | D |
| 122 | $CH_3$ | $CD_3$ | $CD_3$ | H |
| 123 | $CH_3$ | $CD_3$ | $CH_3$ | D |
| 124 | $CH_3$ | $CH_3$ | $CD_3$ | D |
| 125 | $CD_3$ | $CD_3$ | $CD_3$ | H |
| 126 | $CD_3$ | $CH_3$ | $CD_3$ | D |
| 127 | $CH_3$ | $CD_3$ | $CD_3$ | D |
| 128 | $CD_3$ | $CD_3$ | $CD_3$ | D |

In one embodiment of the compound of formula Ia, $R^4$ is

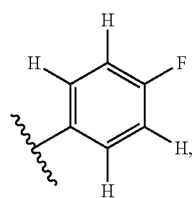

$Y^1$ and $Y^2$ are the same; $R^{2a}$ and $R^{2b}$ are the same; $R^6$ is —$CH_2$—$C(O)$—$CH_2$—$CH_2$—$O$—$CH_3$, and the compound is selected from any one of the compounds set forth in the table below:

| Compound | $R^1$ | $R^{2a}/R^{2b}$ | $R^3$ | $Y^1/Y^2$ |
|---|---|---|---|---|
| 129 | $CD_3$ | $CH_3$ | $CH_3$ | H |
| 130 | $CH_3$ | $CD_3$ | $CH_3$ | H |
| 131 | $CH_3$ | $CH_3$ | $CD_3$ | H |
| 132 | $CH_3$ | $CH_3$ | $CH_3$ | D |
| 133 | $CD_3$ | $CD_3$ | $CH_3$ | H |
| 134 | $CD_3$ | $CH_3$ | $CD_3$ | H |
| 135 | $CD_3$ | $CH_3$ | $CH_3$ | D |
| 136 | $CH_3$ | $CD_3$ | $CD_3$ | H |
| 137 | $CH_3$ | $CD_3$ | $CH_3$ | D |
| 138 | $CH_3$ | $CH_3$ | $CD_3$ | D |
| 139 | $CD_3$ | $CD_3$ | $CD_3$ | H |
| 140 | $CD_3$ | $CH_3$ | $CD_3$ | D |
| 141 | $CH_3$ | $CD_3$ | $CD_3$ | D |
| 142 | $CD_3$ | $CD_3$ | $CD_3$ | D |

In one embodiment, any atom not designated as deuterium is present at its natural isotopic abundance.

The synthesis of compounds of Formula I can be readily achieved by synthetic chemists of ordinary skill.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Certain intermediates can be used with or without purification (e.g., filtration, distillation, sublimation, crystallization, trituration, solid phase extraction, and chromatography).

Exemplary Synthesis

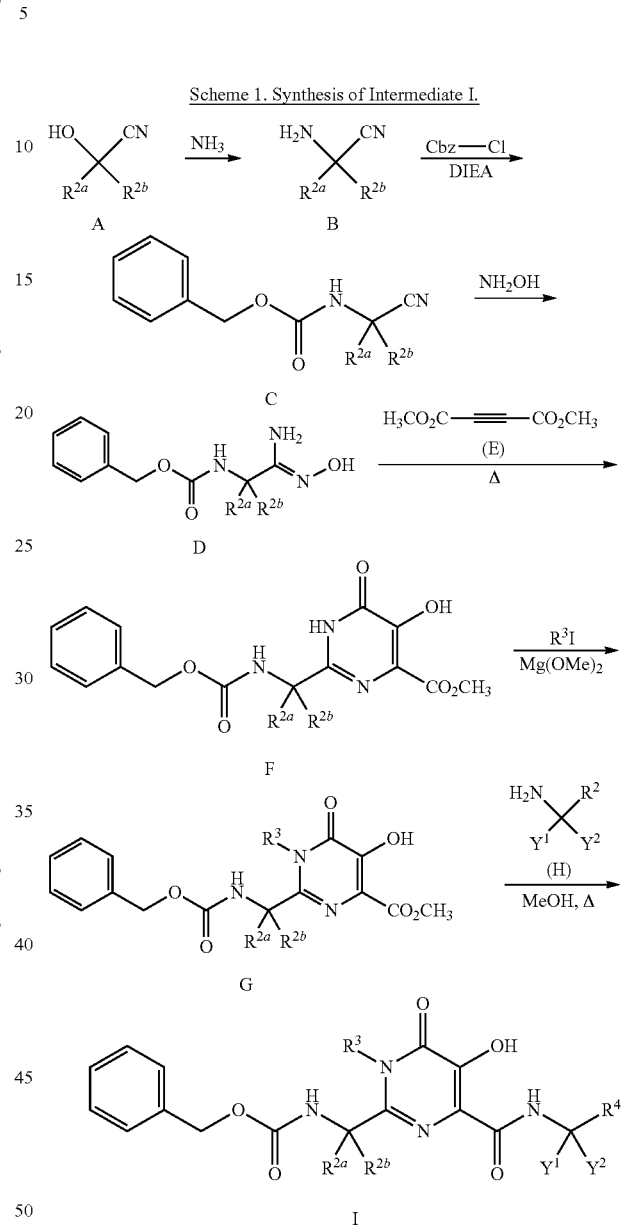

A convenient method for synthesizing intermediate I is depicted in Scheme 1. Compound A is first treated with ammonia to provide B, which is subsequently treated with Cbz-chloride in the presence of diisopropylethylamine to provide carbamate C. The deuterated version of A is prepared from commercially available $D_6$-acetone and potassium cyanide as described by Horino, Y et al., Chem Eur J, 2003, 9(11):2419-2438. C is then allowed to react with hydroxylamine to provide D, which is condensed with dimethyl acetylenedicarboxylate (E) and cyclized to the pyrimidone F. The pyrimidone F is N-alkylated with iodomethane or $D_3$-iodomethane in the presence of magnesium methoxide to provide G, which is converted to amide I by reaction with H. The appropriately deuterated analogs of formula H can be prepared as shown below in Schemes 4a and 4b.

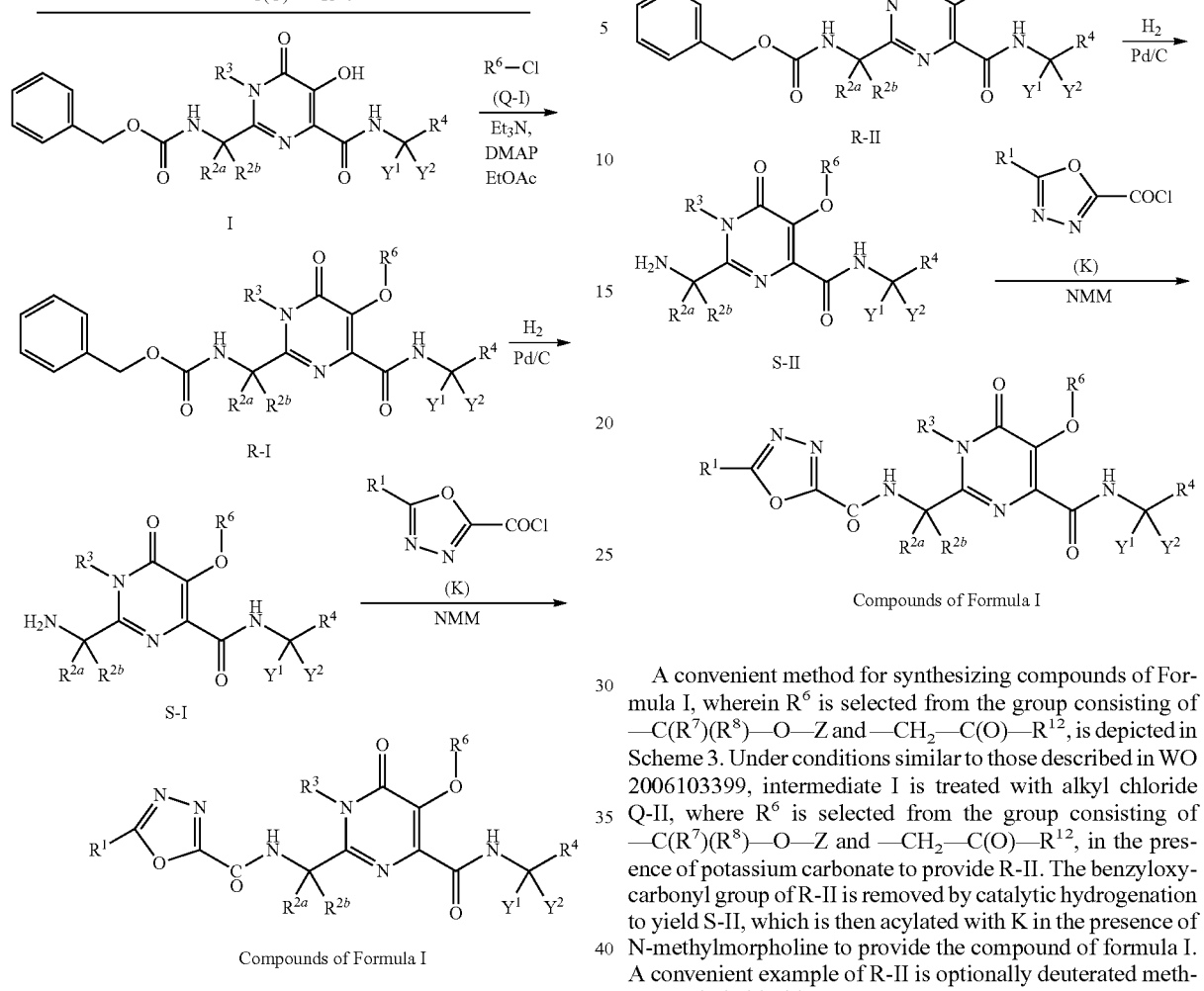

A convenient method for synthesizing compounds of Formula I wherein $R^6$ is —C(O)—$R^{12}$ is depicted in Scheme 2. Under conditions similar to those described in WO 2009088729, I is treated with Q-I wherein $R^6$ is —C(O)—$R^{12}$, wherein q is 0, in the presence of triethylamine and DMAP to provide R-I. The benzyloxycarbonyl group of R-I is removed by catalytic hydrogenation to yield S-I, which is then acylated with K in the presence of N-methylmorpholine to provide the compound of formula I.

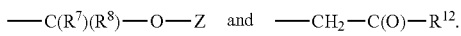

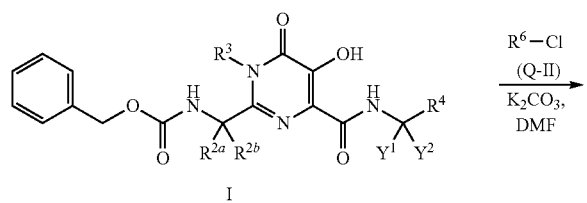

A convenient method for synthesizing compounds of Formula I, wherein $R^6$ is selected from the group consisting of —C($R^7$)($R^8$)—O—Z and —$CH_2$—C(O)—$R^{12}$, is depicted in Scheme 3. Under conditions similar to those described in WO 2006103399, intermediate I is treated with alkyl chloride Q-II, where $R^6$ is selected from the group consisting of —C($R^7$)($R^8$)—O—Z and —$CH_2$—C(O)—$R^{12}$, in the presence of potassium carbonate to provide R-II. The benzyloxycarbonyl group of R-II is removed by catalytic hydrogenation to yield S-II, which is then acylated with K in the presence of N-methylmorpholine to provide the compound of formula I. A convenient example of R-II is optionally deuterated methoxymethyl chloride.

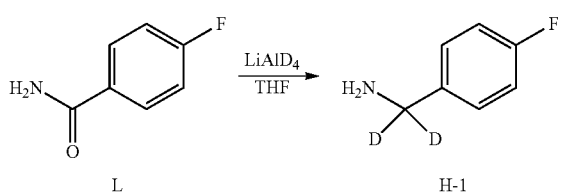

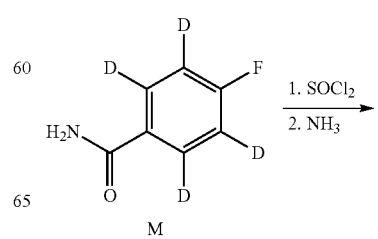

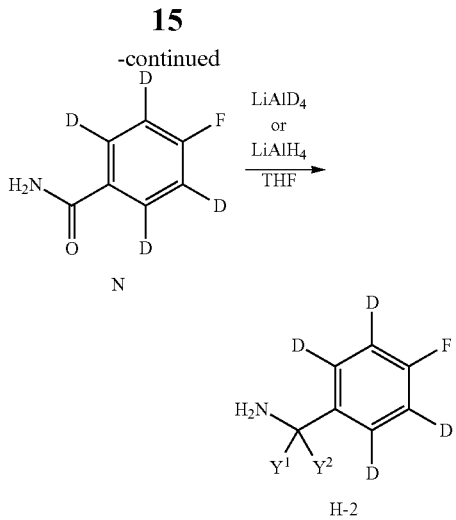

Schemes 4a and 4b depict the synthesis of alternative $R^4$ moieties that may be used in Scheme 1. In Scheme 4a, amide L is reduced to a primary amine H-1 with lithium aluminum deuteride as described for lithium aluminum hydride by Tachibana, Y et al., J Org Chem, 2006, 71(14):5093-5104. H-1 is then used as shown in Scheme 1.

As depicted in Scheme 4b, to produce the D4-aryl version of H(H-2), commercially available M is converted to the acid chloride with thionyl chloride and then treated with ammonia to provide the amide N (see Sardashti, M et al., J Phys Chem, 1988, 92(16):4620-4632). The amide N is converted to the appropriately deuterated amine H-2 using lithium aluminum deuteride or lithium aluminum hydride.

Scheme 5. Synthesis of Compound K.

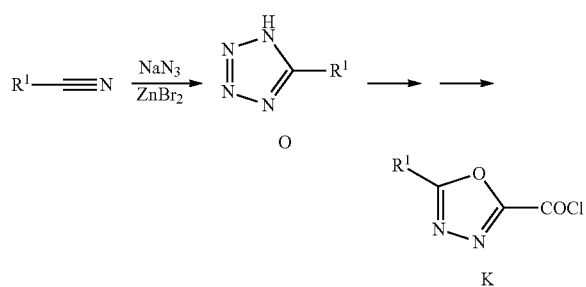

Compound K (cf. Scheme 1) is prepared as provided in Scheme 5 from the deuterated tetrazole 0, which is produced from commercially available deuterated acetonitrile as described by Demko, Z P et al., J Org Chem, 2001, 66(24): 7945-7950 as shown in Scheme 5. The tetrazole is then converted to K using the procedures disclosed in International Publication Number WO2006060712.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of Formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the US Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this disclosure are only those that result in the formation of stable compounds.

Compositions

The disclosure also provides pyrogen-free compositions comprising an effective amount of a compound of Formula I (e.g., including any of the formulae herein), or a pharmaceutically acceptable salt of said compound; and an acceptable carrier. Preferably, a composition of this disclosure is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g. U.S. Pat. No. 6,803,031.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active.

Where an organ or tissue is accessible because of removal from the patient, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with an HIV integrase inhibitor. Such agents include those described in detail in WO 2005/087767, WO 2005/087768, and WO 2006/107478.

In certain embodiments, the second therapeutic agent is any one or more of an antiviral agent (e.g., acyclovir, ganciclovir, or famciclovir), anti-infective, immunomodulator (e.g., granulocyte macrophage colony stimulating factor, gamma interferon, and IL-2), antibiotic (e.g., clindamycin, fluconazole, pentamidine, and trimethoprim), CCR5 receptor antagonist (e.g., maraviroc, vicriviroc, PRO-140 and TAK-220), vaccine, HIV protease inhibitor (e.g., indinavir, ritonavir, darunavir or nelfinavir), nucleoside reverse transcriptase inhibitor or non-nucleoside reverse transcriptase inhibitor (e.g., etravirine, azidothymidine (AZT) or efavirenz).

In one embodiment, the second therapeutic agent is selected from one or more of darunavir, ritonavir, and etravirine.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this disclosure can range from about 0.01 to about 500 mg/kg body weight per day orally in a single dose or in divided doses. Another preferred dosage range is about 0.1 to about 100 mg/kg body weight per day orally in single or divided doses. A more specific dosage range is from about 1 to about 25 mg/kg body weight. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for raltegravir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Methods of Treatment

In another embodiment, the disclosure provides a method of modulating the activity of HIV integrase in an HIV-infected cell, comprising contacting the cell with one or more compounds of Formula I herein or pharmaceutically acceptable salts thereof.

According to another embodiment, the disclosure provides a method of treating a patient suffering from, or susceptible to, an HIV infection and the prevention, treatment or the delay in the onset of consequent pathological conditions such as AIDS. This includes, but is not limited to, treatment of a wide range of states of HIV infection: AIDS, ARC (AIDS related complex), both symptomatic and asymptomatic, and actual or potential exposure to HIV. For example, the compounds of this disclosure are useful in treating infection by HIV after suspected past exposure to HIV by such means as blood transfusion, exchange of body fluids, bites, accidental needle stick, or exposure to patient blood during surgery.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with raltegravir. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include co-administering a compound of Formula I or a pharmaceutically acceptable salt thereof and a second therapeutic agent selected from one or more of darunavir, ritonavir, and etravirine.

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a patient does not preclude the separate administration of that same therapeutic agent, any other second therapeutic agent or any compound of this disclosure to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In yet another aspect, the disclosure provides the use of a compound of Formula I or a pharmaceutically acceptable salt thereof alone or together with one or more of the above-described second therapeutic agents in the manufacture of a medicament, either as a single composition or as separate dosage forms, for treatment or prevention in a patient of a disease, disorder or symptom set forth above. Another aspect of the disclosure is a compound of Formula I for use in the treatment or prevention in a patient of a disease, disorder or symptom thereof delineated herein.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay:

The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

Experimental Procedures:

Human liver microsomes are obtained from a commercial source (e.g., Absorption Systems L.P. (Exton, Pa.)). The incubation mixtures are prepared as follows:

| Reaction Mixture Composition | |
|---|---|
| Liver Microsomes | 1.0 mg/mL |
| NADPH | 1 mM |
| Potassium Phosphate, pH 7.4 | 100 mM |
| Magnesium Chloride | 10 mM |
| Test Compound | 1 μM. |

Incubation of Test Compounds with Liver Microsomes:

The reaction mixture, minus cofactors, is prepared. An aliquot of the reaction mixture (without cofactors) is incubated in a shaking water bath at 37° C. for 3 minutes. Another aliquot of the reaction mixture is prepared as the negative control. The test compound is added into both the reaction mixture and the negative control at a final concentration of 1 μM. An aliquot of the reaction mixture is prepared as a blank control, by the addition of plain organic solvent (no test compound). The reaction is initiated by the addition of cofactors (not added to the negative controls), and then incubated in a shaking water bath at 37° C. Aliquots (200 μL) are withdrawn in triplicate at multiple time points (e.g., 0, 15, 30, 60, and 120 minutes) and combined with 800 μL of ice-cold 50/50 acetonitrile/dH$_2$O to terminate the reaction. The positive controls, testosterone and propranolol, as well as raltegravir, are each run simultaneously with the test compounds in separate reactions.

All samples are analyzed using LC-MS (or MS/MS). An LC-MRM-MS/MS method is used for metabolic stability.

Also, Q1 full scan LC-MS methods are performed on the blank matrix and the test compound incubation samples. The Q1 scans serve as survey scans to identify any sample unique peaks that might represent the possible metabolites. The masses of these potential metabolites can be determined from the Q1 scans.

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

I claim:

1. A compound of Formula I-A:

(I-A)

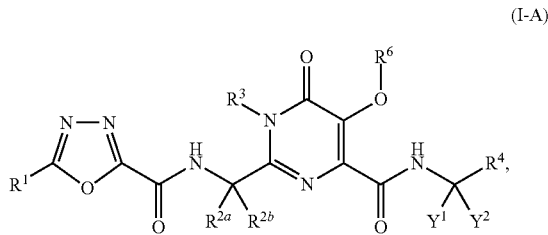

or a pharmaceutically acceptable salt thereof, wherein:
each of $R^1$, $R^{2a}$, $R^{2b}$, and $R^3$ is independently selected from —$CH_3$, —$CDH_2$, —$CD_2H$, and —$CD_3$;
$Y^1$ and $Y^2$ are each independently selected from H and D;
$R^4$ is selected from:

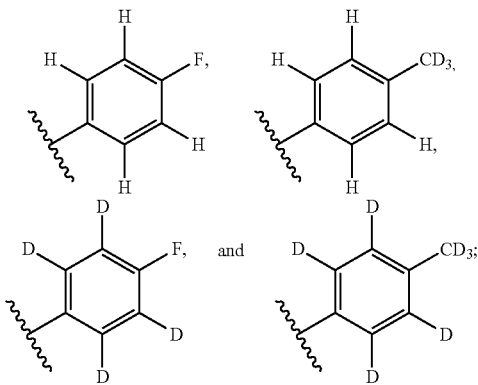

and
$R^6$ is selected from the group consisting of —$C(R^7)(R^8)$—O—Z and —$(CH_2)_q$—C(O)—$R^{12}$, wherein:
q is 1 or 0;
$R^{12}$ is $C_6$-$C_{10}$ aryl optionally substituted with deuterium, or $C_1$-$C_7$ alkyl optionally substituted with one or two $R^{10}$ and further optionally substituted with deuterium, wherein
(a)(i) one carbon unit in the $C_1$-$C_7$ alkyl, wherein the carbon unit is bound to a —C(O)— of the —C(O)—$C_1$-$C_7$ alkyl, is optionally replaced with —C(O)—, —O—, —S—, —NH, or —N($C_1$-$C_3$ alkyl);

a(ii) one carbon unit in the $C_1$-$C_7$ alkyl, wherein the carbon unit is not bound to a —C(O)— of the —C(O)—$C_1$-$C_7$ alkyl, is optionally replaced with —C(O)—, —S(O)—, —$S(O)_2$, —O—, —S—, —NH, or —N($C_1$-$C_3$ alkyl);

(b)(i) when a first carbon unit in the $C_1$-$C_7$ alkyl is replaced with —C(O)—, —S(O)—, or —$S(O)_2$, a second carbon unit is optionally replaced with —O—, —S—, —NH, or —N($C_1$-$C_3$ alkyl); and (b)(ii) when a first carbon unit in the $C_1$-$C_7$ alkyl is replaced with —O—, —S—, —NH, or —N($C_1$-$C_3$ alkyl), a second carbon unit, separated by at least two carbon units from the first carbon unit replaced with —O—, —S—, —NH, or —N($C_1$-$C_3$ alkyl), is optionally replaced with —O—, —S—, —NH, or —N($C_1$-$C_3$ alkyl);

each $R^{10}$ is independently a $C_3$-$C_7$ carbocyclyl or a 3-7-membered heterocyclyl, wherein each $R^{10}$ is optionally and independently substituted with $C_1$-$C_3$ alkyl or deuterium and optionally and independently benzofused;

$R^7$ and $R^8$ are each independently hydrogen, deuterium, or $C_1$-$C_3$ alkyl optionally substituted with deuterium; or $R^7$ and $R^8$ taken together with the carbon to which they are attached form a $C_3$-$C_7$ saturated or partially saturated carbocyclic ring or a saturated or partially saturated 3-7-membered heterocyclic ring, wherein the carbocyclic ring or heterocyclic ring is optionally substituted with deuterium; and Z is $C_1$-$C_6$ alkyl optionally substituted with deuterium, provided that when each of $Y^1$ and $Y^2$ is H, then at least one of $R^1$, $R^{2a}$, $R^{2b}$, $R^3$ and $R^4$ comprises deuterium.

2. A compound of claim 1, wherein $R^6$ is —$(CH_2)_q$—C(O)—$R^{12}$, wherein q is 1 or 0; and $R^{12}$ is —$C_1$-$C_7$ alkyl optionally substituted with one $R^{10}$ and further optionally substituted with deuterium, wherein each $R^{10}$ is optionally and independently substituted with $C_1$-$C_3$ alkyl or deuterium, and wherein the first and the second carbon units in (b)(ii) are each optionally replaced with —O—.

3. A compound of claim 1 or 2, wherein $R^{12}$ is isobutyl, neopentyl, isoamyl, —$CH_2$—$CH_2$—O—$CH_3$, —$CH_2$—$CH_2$—O—$CH_2$—$CH_2$—O—$CH_3$,

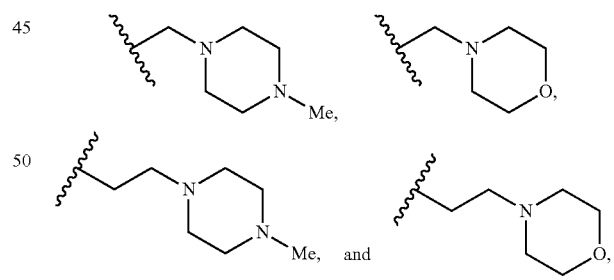

wherein $R^{12}$ and the heterocyclyl substituent of $R^{12}$ are each optionally and independently substituted with deuterium.

4. A compound of claim 1, wherein each of $R^1$, $R^{2a}$, $R^{2b}$, and $R^3$ is independently selected from —$CH_3$ and —$CD_3$.

5. A compound of claim 1 or 4, wherein $Y^1$ and $Y^2$ are the same.

6. A compound of claim 5, wherein each of $Y^1$ and $Y^2$ is hydrogen.

7. A compound of claim 1 or 4, wherein $R^{2a}$ and $R^{2b}$ are the same and are selected from —$CH_3$ and —$CD_3$.

8. A compound of claim 1 or 4, wherein $R^4$ is selected from

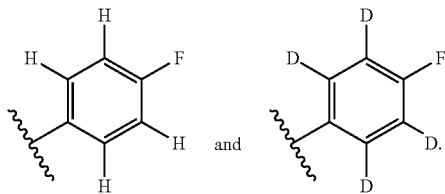

9. A compound of claim 1, wherein $R^4$ is

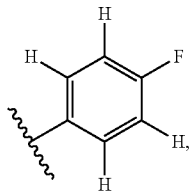

$Y^1$ and $Y^2$ are the same; $R^{2a}$ and $R^{2b}$ are the same; $R^6$ is —C(O)—CH$_2$—CH$_2$—O—CH$_3$, and the compound is selected from any one of the compounds set forth in the table below:

| Compound | $R^1$ | $R^{2a}/R^{2b}$ | $R^3$ | $Y^1/Y^2$ |
|---|---|---|---|---|
| 101 | CD$_3$ | CH$_3$ | CH$_3$ | H |
| 102 | CH$_3$ | CD$_3$ | CH$_3$ | H |
| 103 | CH$_3$ | CH$_3$ | CD$_3$ | H |
| 104 | CH$_3$ | CH$_3$ | CH$_3$ | D |
| 105 | CD$_3$ | CD$_3$ | CH$_3$ | H |
| 106 | CD$_3$ | CH$_3$ | CD$_3$ | H |
| 107 | CD$_3$ | CH$_3$ | CH$_3$ | D |
| 108 | CH$_3$ | CD$_3$ | CD$_3$ | H |
| 109 | CH$_3$ | CD$_3$ | CH$_3$ | D |
| 110 | CH$_3$ | CH$_3$ | CD$_3$ | D |
| 111 | CD$_3$ | CD$_3$ | CD$_3$ | H |
| 112 | CD$_3$ | CH$_3$ | CD$_3$ | D |
| 113 | CH$_3$ | CD$_3$ | CD$_3$ | D |
| 114 | CD$_3$ | CD$_3$ | CD$_3$ | D. |

10. A compound of claim 1 or claim 4, wherein any atom not designated as deuterium is present at its natural isotopic abundance.

11. A pyrogen-free pharmaceutical composition comprising a compound of claim 1 or claim 4 and a pharmaceutically acceptable carrier.

12. The composition of claim 11, further comprising a second therapeutic agent selected from an antiviral agent, an anti-infective, an immunomodulator, an antibiotic, a CCR5 receptor antagonist, a vaccine, a viral protease inhibitor, a nucleoside reverse transcriptase inhibitor and a non-nucleoside reverse transcriptase inhibitor.

13. The composition of claim 12, wherein the second therapeutic agent is selected from one or more of darunavir, ritonavir, and etravirine.

* * * * *